United States Patent [19]
Takeuchi

[11] 3,962,922
[45] June 15, 1976

[54] SAMPLING APPARATUS FOR FLUID

[75] Inventor: Kazuhiko Takeuchi, Fujisawa, Japan

[73] Assignee: Honeywell Inc., Minneapolis, Minn.

[22] Filed: Jan. 30, 1975

[21] Appl. No.: 545,545

[52] U.S. Cl.................................. 73/424; 73/215
[51] Int. Cl.².......................................... G01N 1/00
[58] Field of Search.................. 73/215, 424, 421 B

[56] References Cited
UNITED STATES PATENTS

| | | | |
|---|---|---|---|
| 2,164,498 | 7/1939 | Clark............................. | 73/421 B |
| 2,270,511 | 1/1942 | Crain............................. | 73/421 B |

*Primary Examiner*—Donald O. Woodiel
*Attorney, Agent, or Firm*—Laurence J. Marhoefer; Lockwood D. Burton

[57] ABSTRACT

Fluid flowing in an open channel or aqueduct having a notched dam or weir produces a hydraulic head at the weir which is proportional to the rate of flow of the fluid in the aqueduct. A sampling device is provided in association with the aqueduct just upstream from the weir which is adapted to scoop up a sample of the flowing fluid in a quantity which is proportional to the hydraulic head. That quantity of fluid may then be measured as a function of the flow rate.

1 Claim, 6 Drawing Figures

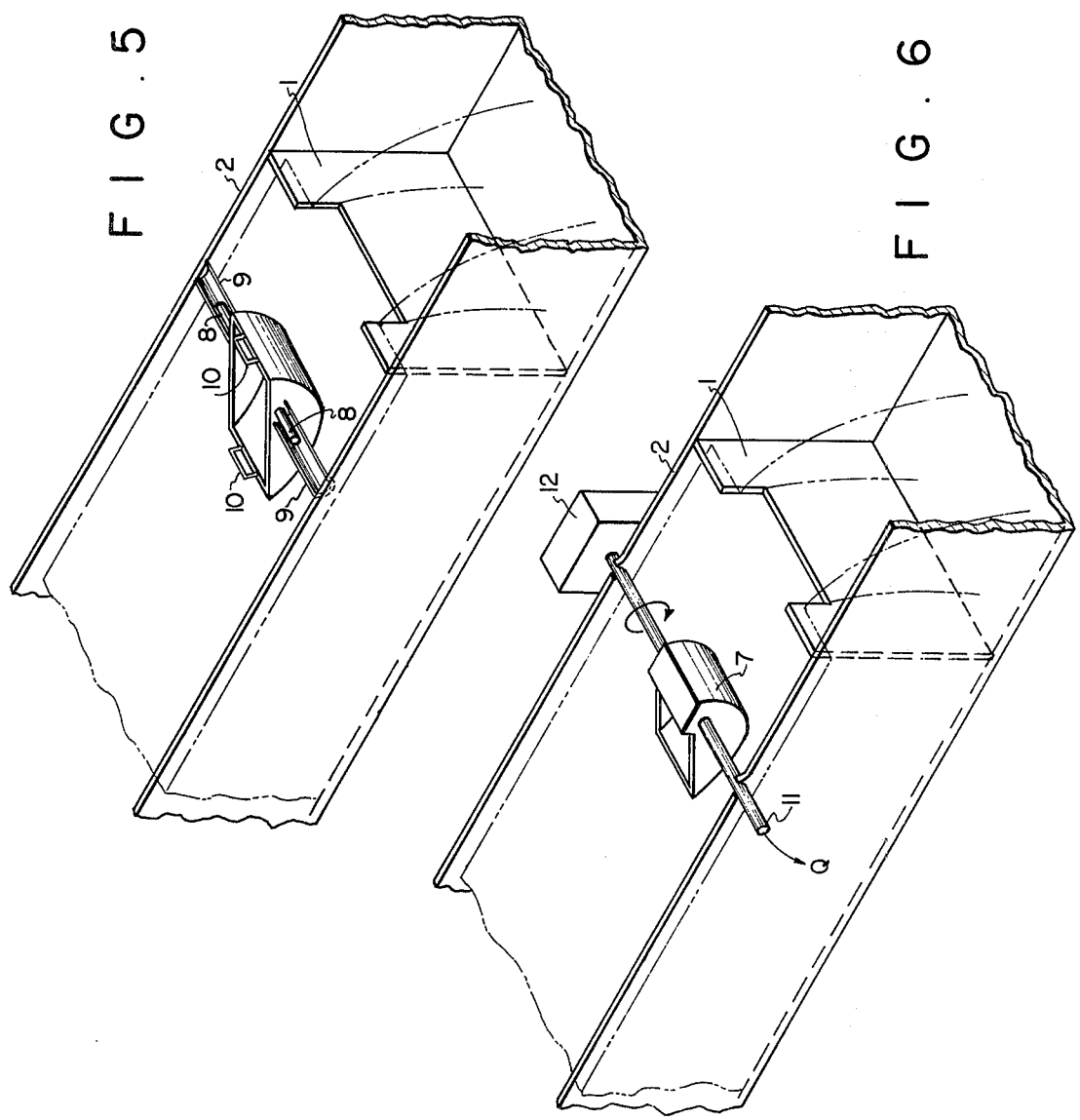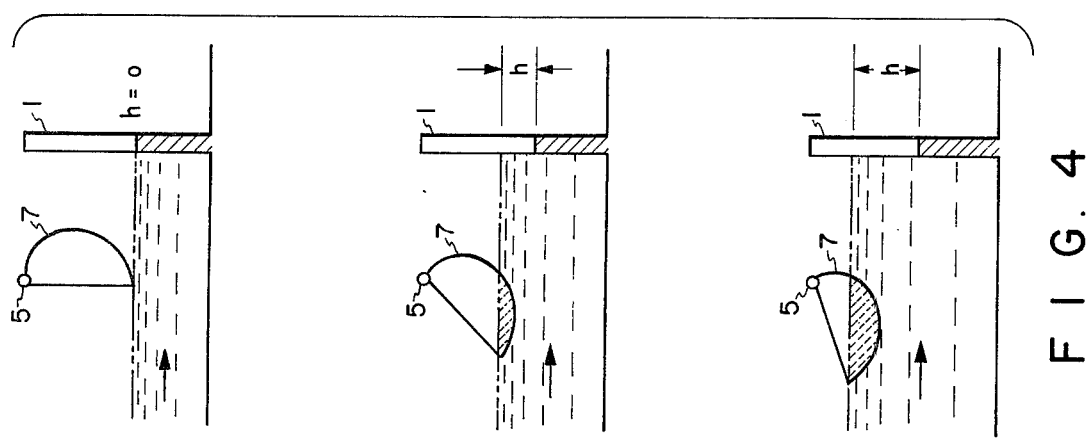

SAMPLING APPARATUS FOR FLUID

BACKGROUND OF THE INVENTION

The present invention relates to a sampling apparatus for fluids. More particularly, it relates to a sampling apparatus capable of obtaining a sample, the quantity of which is proportional to the total flow of the fluid.

When a fluid is flowing in an open channel or aqueduct and the flow is obstructed by a notched dam or weir, the height of the head above the edge of the weir is determined by the rate of flow of the fluid. Thus, the flow rat may be calculated as a function of the head in accordance with the general equation:

$$F = f(h) \tag{1}$$

where $F$ represents the volume rate of flow of the fluid and $h$ represents the height of the head. In a well-known dam or weir type flowmeter, the function $f(h)$ will be expressed by the simple relationship with regard to $h$, as follows:

$$F = f(h) = Kh^n \tag{2}$$

where
- $K$ — a coefficient for flow quantity;
- $n$ — an index number defined in accordance with the cross-sectional shape of the weir or notch in the dam ($n = 5/2$ when the cross-section is triangular while $n = 3/2$ when it is rectangular).

Assume, now, that the following relation is achieved between Q and $k$, where Q is the volume of a fluid sample and $k$ is a constant:

$$Q = k \cdot f(h) \tag{3}$$

Accordingly, from equations (1) and (3), we obtain:

$$Q = k \cdot F \tag{4}$$

This equation shows that the volume of a sampled quantity can be proportional to the flow rate of the fluid in the open channel or aqueduct.

SUMMARY OF THE INVENTION

It is, accordingly, an object of the present invention to provide an improved fluid flow measuring means for measuring the flow of fluid in an open channel or aqueduct.

It is another object of the present invention to provide an improved fluid flow measuring means as set forth and featuring means for obtaining samples from the flowing fluid, the volume of which is proportional to the volume flow rate of the fluid.

In accomplishing these and other objects, there has been provided, in accordance with the present invention, a sampling scoop positioned in relation to an open channel adjacent a weir therein such that as the scoop is rotated to take a sample of the fluid from the aqueduct, the quantity of the fluid picked-up by the scoop is a function of the height of the fluid in the aqueduct above the bottom of the notch in the weir.

BRIEF DESCRIPTION OF THE DRAWINGS

A better understanding of the invention may be had from the following detailed description when read in association with the accompanying drawings in which:

FIG. 4 is a series of diagrams further illustrating the operation of the present invention;

FIG. 5 is a perspective view of a particular embodiment of the present invention; and FIG. 6 is a perspective view of a different structure also embodying the present invention.

DETAILED DESCRIPTION

Figure 1:
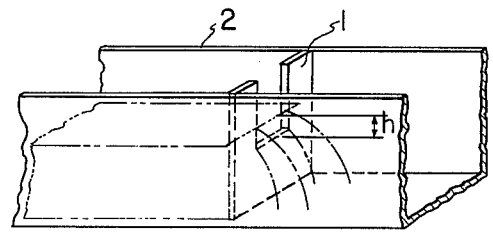
FIG. 1 is a perspective view of a dam or weir type flowmeter.

Referring now to the drawings in more detail, there is shown in FIG. 1 a notched dam or weir 1 positioned across an open channel or aqueduct 2 through which a fluid is adapted to flow. As the fluid flows through the aqueduct or channel, the level of the fluid on the upstream side of the dam will build up to a height $h$ proportional to the volume flow rate of the fluid.

Figure 2:
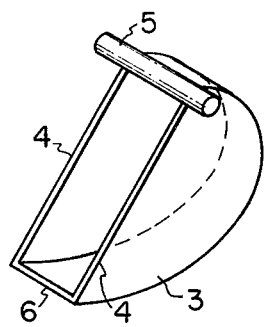
FIG. 2 is a perspective view of a sampling scoop embodying the present invention.

In FIG. 2 there is shown a sampling scoop embodying the present invention. The sampling scoop includes a curved bottom plate 3 sandwiched between two plain parallel sides 4 leaving a relatively straight open upper surface. Adjacent one end of the open upper portion there is provided a pivot member 5 about which the sampler may be rotated. The opposite end of the open surface, with respect to the pivot member 5, defines a leading edge 6 of the sampling scoop.

Figure 3:
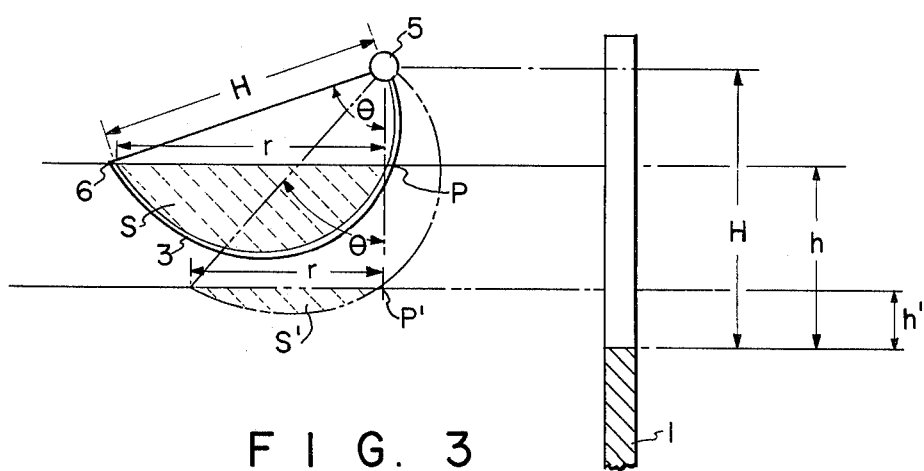
FIG. 3 is a diagram illustrating the operating principle of the present invention.

In FIG. 3 there is shown a diagrammatic representation of means for obtaining the curvature for the bottom plate 3 in accordance with the present invention. First, the sampling scoop is positioned relative to the channel or aqueduct 2 such that the distance H from the center of rotation of the axis 5 to the lip of the notch at the bottom of the weir 1 is equal to the distance H from the center of rotation of the axis 5 to the edge of the lip 6 of the scoop, and positioned on the upstream side of the weir. A line drawn from the center of rotation of the axis 5 to the edge of the lip 6 (which in the illustrative example coincides with the upper edge of the scoop) subtends an angle $\theta$ with a vertical line drawn from the center of the axis 5 to the surface of the fluid in the aqueduct. As the fluid in the aqueduct changes height with changes in flow rate, that fluid will establish a level at a distance $h$, $h'$ . . . above the bottom of the notch in the weir 1. If the forward lip 6 of the scoop is rotated about the axis 5 to a position whereat the lip 6 coincides with the surface of the fluid then the fluid in the scoop, at the same level as the fluid in the aqueduct, will define a surface $s$, $s'$ having a length $r$, $r'$ extending from the lip 6 to the point P, P' where the fluid level intersects the inner surface of the bottom plate 3. With the foregoing structural relationships, it may be seen that:

$$\cos \theta = \frac{H - h}{H}$$

$$h = H(1 - \cos \theta) \tag{5}$$

The surfaces S, S' . . . represented by the shaded portions, which vary in accordance with the fluid level, are approximated by the equation:

$$S = \int_0^\theta \tfrac{1}{2} r^2 \, d\theta \tag{6}$$

Since equation (6) is proportional to equation (5), in the case of a dam or weir having a rectangularly shaped notch, $$S = \int_o^\theta \tfrac{1}{2} r^2 \, d\theta \propto h^{3/2} = H^{3/2} (1 - \cos \theta)^{3/2}$$

From this equation, $$\tfrac{1}{2} r^2 \propto (3/2) H^{3/2} (1 - \cos \theta)^{1/2} \cdot \sin \theta$$

$$r(\theta) \propto \sqrt{\sin \theta} \cdot \sqrt[4]{1 - \cos \theta}$$

$$r(\theta) - K \cdot \sqrt{\sin \theta} \cdot \sqrt[4]{1 - \cos \theta} \qquad (7)$$

By this equation (7), points P, P' ... are plotted by using the distances r, r' ... calculated for each inclination angle θ, θ' ... corresponding to the height h, h' ... of the fluid in the aqueduct.

With reference to FIG. 4, it may be seen that as the sampling scoop 7 is rotated slowly about the axis 5, with the open side of the sampling scoop 7 directed upstream, the quantity Q of fluid taken into the sampler on any selected rotation will be determined by the height h of the fluid level. Accordingly, it may be seen that with the sampling scoop of the present invention, one may intermittently obtain a sample of the fluid flowing in the aqueduct or channel, the quantity Q of which sample is proportional to the instantaneous fluid flow rate. When the sampling scoop is designed, as hereinbefore set forth, the relationship between the quantity Q of the sampled fluid and the height of the flowing fluid will be as expressed in equation (3).

In FIG. 5 there is shown an example of a particular embodiment of a sampler 7 constructed in accordance with the present invention. There, the sampler scoop 7 is provided with a pair of shafts 8 concentric with the rotation axis thereof. The shafts 8 are secured and project outwardly from opposite sides of the two side walls of the sampling scoop. A pair of support or receiving members 9 having a semi-circular cross-section are secured to and extend inwardly from the side walls of the aqueduct or channel 2. They are so positioned that when the projections 8 of the scoop 7 are positioned and received in the receiving members 9, the scoop will be positioned relative to the notch in the weir in accordance with the foregoing description. A pair of handles 10 are provided at opposite ends of the scoop whereby the scoop may be manually rotated about its axis to acquire a sample as hereinbefore described. By means of the handles 10, the scoop 7 may be removed from its operating position and the contents thereof poured out into a suitably calibrated measuring device whereby the measured sample will be indicative of the flow rate of the fluid in the channel.

In FIG. 6 there is shown another embodiment of the present invention in which the sampling scoop 7 is supported in the appropriate position relative to the channel 2 and the notch in the weir 1 by a hollow cylindrical shaft 11. One end of the shaft 11 is connected in driving relation to a driving motor 12. The driving motor 12 may be programmed to drive the shaft 11 and, thereby, the sampling scoop 7, through one complete revolution at predetermined intervals whereby to effect sampling of the fluid on each such revolution. The end of the shaft 11 which extends between the sampling scoop 7 and the driving motor 12 may be plugged or otherwise blocked to prevent fluid from entering that portion of the interior of the shaft. The end of the hollow shaft 11 remote from the driving motor 12 is opened to the fluid within the scoop and is so arranged that as the sample of the fluid is obtained the fluid contained therein flows out from the scoop either by gravity or by means of an auxiliary pump (not shown) to suitable measuring means.

While both the notch in the weir and the cross-section of the sampling scoop are both shown in the illustrative embodiment as being rectangular, it should be noted that the invention is not limited to that configuration but is applicable to any configuration wherein the effective construction of the sampler will satisfy the relationship given in equation (3) as hereinbefore given. Thus, it may be seen that there has been provided, in accordance with the present invention, an improved fluid flow measuring means for measuring the flow of fluid in an open channel or aqueduct and includes means for obtaining samples from the flowing fluid, the volume of which sample is proportional to the volume flow rate of the fluid.

What is claimed is:
1. A sampling apparatus for sampling a fluid flowing in an open aqueduct provided with a notched weir in which the relation $F = f(h)$ prevails where $F$ is the volume flow rate and $h$ is the height of fluid level above the bottom of the notch in the weir; the improvement comprising:
   a rotatable sampling scoop means,
   means for supporting said sampling scoop means on an axis of rotation positioned a predetermined distance above the level of the bottom of the notch in said weir and on the upstream side of said weir,
   said sampling scoop means having a forward edge at a distance from said axis of rotation equal to the distance from said axis of rotation above the level of the bottom of said notch in said weir,
   said sampling scoop means being configured to satisfy the relation $Q = k \cdot F$, where $Q$ is the quantity of fluid in a sample obtained by said sampling scoop means when said scoop means is rotated about said axis, $k$ is a proportionality constant and $F$ is the volume flow rate.

* * * * *